US012575747B2

(12) United States Patent
Cao et al.

(10) Patent No.: US 12,575,747 B2
(45) Date of Patent: Mar. 17, 2026

(54) AIR CONTROL MECHANISM AND SPHYGMOMANOMETER

(71) Applicant: SHENZHEN JAMR TECHNOLOGY CO., LTD., Shenzhen (CN)

(72) Inventors: Yingxiang Cao, Shenzhen (CN); Liming Wang, Shenzhen (CN)

(73) Assignee: SHENZHEN JAMR TECHNOLOGY CO., LTD., Shenzhen (CN)

( * ) Notice: Subject to any disclaimer, the term of this patent is extended or adjusted under 35 U.S.C. 154(b) by 375 days.

(21) Appl. No.: 18/448,126

(22) Filed: Aug. 10, 2023

(65) Prior Publication Data

US 2024/0245310 A1    Jul. 25, 2024

(51) Int. Cl.
| | |
|---|---|
| *A61B 5/021* | (2006.01) |
| *A61B 5/022* | (2006.01) |
| *A61B 5/0235* | (2006.01) |
| *F04B 45/047* | (2006.01) |

(52) U.S. Cl.
CPC .......... *A61B 5/02141* (2013.01); *A61B 5/022* (2013.01); *A61B 5/0235* (2013.01); *F04B 45/047* (2013.01)

(58) Field of Classification Search
CPC ... A61B 5/02141; A61B 5/022; A61B 5/0235; F04B 45/047
USPC ...................... 417/413.1, 415, 472, 473, 521
See application file for complete search history.

(56) References Cited

U.S. PATENT DOCUMENTS

| | | | | | |
|---|---|---|---|---|---|
| 3,613,668 | A | * | 10/1971 | Beck ..................... | A61B 5/0235 |
| | | | | | D24/166 |
| 3,828,811 | A | * | 8/1974 | Natkanski ................. | F16K 3/34 |
| | | | | | 251/304 |
| 4,690,171 | A | * | 9/1987 | Johnston .............. | A61B 5/0235 |
| | | | | | 137/625.48 |
| 4,801,249 | A | * | 1/1989 | Kakizawa ........... | F04B 43/0018 |
| | | | | | 92/48 |
| 5,027,823 | A | * | 7/1991 | Sanaka ................ | A61B 5/0235 |
| | | | | | 137/513.5 |
| 5,092,338 | A | * | 3/1992 | Ide ......................... | A61B 5/022 |
| | | | | | 600/490 |
| 5,137,024 | A | * | 8/1992 | Souma ................. | A61B 5/0235 |
| | | | | | 137/513.5 |
| 5,476,367 | A | * | 12/1995 | Zimmermann ......... | F04B 49/24 |
| | | | | | 417/415 |

(Continued)

FOREIGN PATENT DOCUMENTS

| | | | | | |
|---|---|---|---|---|---|
| CN | | 212297732 U | * | 1/2021 | |
| WO | WO-2015109924 A1 | * | 7/2015 | ........... | A61B 5/0235 |

OTHER PUBLICATIONS

Translation of CN 212297732, YEAR 2015.*

*Primary Examiner* — William M McCalister

(74) *Attorney, Agent, or Firm* — Hemisphere Law, PLLC

(57) ABSTRACT

An air control mechanism and a sphygmomanometer including the air control mechanism are provided. The air control mechanism includes a first housing, a second housing, a tower-shaped piston, and an intake-exhaust mechanism. In an intake state, air in the first chamber sequentially flows through the flow groove, presses against the elastic thin plate, flows through the stepped hole and flows to the exhaust passage through the guiding groove. In an exhaust state, air sequentially flows through the flow passage and the exhaust passage to the guiding groove.

10 Claims, 9 Drawing Sheets

(56) References Cited

U.S. PATENT DOCUMENTS

| | | | | |
|---|---|---|---|---|
| 6,382,928 B1* | 5/2002 | Chang | .................... | F04B 43/026 |
| | | | | 417/269 |
| 2002/0051717 A1* | 5/2002 | Fukami | .................... | F04B 43/04 |
| | | | | 417/413.1 |
| 2004/0186385 A1* | 9/2004 | Mochizuki | ......... | A61B 5/02141 |
| | | | | 600/499 |
| 2004/0225224 A1* | 11/2004 | Tseng | ................. | A61B 5/02141 |
| | | | | 600/499 |
| 2007/0140879 A1* | 6/2007 | Huang | ................. | F04B 45/022 |
| | | | | 417/472 |
| 2011/0028853 A1* | 2/2011 | Sano | ........................ | F16K 15/16 |
| | | | | 600/490 |
| 2012/0165687 A1* | 6/2012 | Sawanoi | ................ | A61B 5/022 |
| | | | | 600/499 |
| 2016/0150984 A1* | 6/2016 | Kandori | ............ | A61B 5/02241 |
| | | | | 600/490 |
| 2020/0352454 A1* | 11/2020 | Sano | .................... | F16K 31/0655 |

* cited by examiner

10 compression
and air intake

1

AIR CONTROL MECHANISM AND SPHYGMOMANOMETER

CROSS-REFERENCE TO RELATED APPLICATIONS

The present application claims foreign priority of Chinese Patent Application No. 2023210507746, filed on May 4, 2023, and Chinese Patent Application No. 2023201953409, filed on Jan. 20, 2023, in the China National Intellectual Property Administration, the contents of all of which are hereby incorporated by reference.

TECHNICAL FIELD

The present disclosure relates to a field of medical devices, in particular to an air control mechanism and a sphygmomanometer.

BACKGROUND

The existing sphygmomanometer is generally provided with an air pump, an electromagnetic valve, a leakage valve and other structures to form an airway. Generally, during use of the sphygmomanometer, the electromagnetic valve is powered on to close the airway, and the cuff is inflated by the air pump. The air pump stops working until the cuff is inflated to a certain pressure. Then the leakage valve is opened to slowly deflate the cuff, during which the sphygmomanometer detects the blood pressure pulse signal and records the blood pressure value. Finally, the electromagnetic valve is powered off to exhaust the air in the cuff quickly. In this way, a blood pressure measurement is completed.

In the sphygmomanometer, an electromagnetic valve, an air pump, a leakage valve and an air pipe are provided, which makes the whole device undesirably large, while miniaturization design of the sphygmomanometer is desirable. Besides, electric energy is inevitably required to control the valve, which hardly meets the requirements of energy conservation and environmental protection.

SUMMARY

To overcome the defects of the existing sphygmomanometer, the present disclosure aims to provide an air control mechanism and a sphygmomanometer, which has a simplified the structure without using an electromagnetic valve and meets the requirements of energy conservation and environmental protection.

According to embodiments of the present disclosure, an air control mechanism is provided. The air control mechanism includes a first housing, a second housing, a tower-shaped piston, and an intake-exhaust mechanism.

The first housing has a flow passage configured to be connected to a cuff.

The second housing is connected to the first housing. An end surface of the first housing facing the second housing defines a flow groove, and an end surface of the second housing facing the first housing defines a guiding groove.

The tower-shaped piston has at least one first chamber in communication with the flow groove. The piston is mounted to the second housing and disposed between the first housing and the second housing. The piston defines an exhaust passage extending along an axis of the piston and communicating with the flow passage. A side surface of the piston facing the first house defines at least one stepped hole. The stepped hole has one end communicating with the guiding groove and one other end spaced apart from the flow groove. The piston is provided with an elastic thin plate at a periphery of the stepped hole.

The intake-exhaust mechanism is configured to intake airflow toward the flow passage or exhaust airflow along the flow passage to the exhaust passage. The intake-exhaust mechanism is configured in such a way that in an intake state, air in the first chamber sequentially flows through the flow groove, presses against the elastic thin plate, flows through the stepped hole and flows to the exhaust passage through the guiding groove, and in an exhaust state, air sequentially flows through the flow passage and the exhaust passage to the guiding groove.

In some embodiments, the guiding groove includes a guiding hole and a plurality of guiding units arranged around the guiding hole. The guiding hole has one end communicating with the exhaust passage and one other end communicating with the intake-exhaust mechanism. A number of the guiding units is equal to a number of the first chambers, and is equal to a number of the flow grooves (130).

In some embodiments, the intake-exhaust mechanism includes a drive motor and a seal adjusting mechanism, and the drive motor has an output shaft. The seal adjusting mechanism includes an eccentric rotor and an elastic seal adjusting mechanism. The eccentric rotor has one end connected to the output shaft and one other end provided with an annular installation groove. The annular installation groove spirally extends along an axis of the eccentric rotor. A transmission wing is provided between the eccentric rotor and the elastic seal adjusting mechanism. The transmission wing has one end received in the annular installation groove and slidably engaged with the annular installation groove, and one other end facing the elastic seal adjusting mechanism. The elastic seal adjusting mechanism has one end facing away from the transmission wing and facing the guiding hole. The transmission wing is configured to be driven by the driving motor in such a way that one end of the elastic sealing adjusting mechanism seals the guiding hole or moves away from the guiding hole.

In some embodiments, the transmission wing includes a housing and a rotating column connected to the housing. The rotating column has one end inserted into the annular installation groove. The driving motor is configured to rotate the eccentric rotor in such a way that the rotating column presses the housing to move upward or downward so that the elastic seal adjustment mechanism seals the guiding hole or moves away from the guiding hole.

In some embodiments, an end surface of the housing facing away from the rotating column is provided with an abutting protrusion. The elastic seal adjusting mechanism includes a main body and a pressing tab disposed at a middle of the main body. The main body has one end facing away from the pressing tab and facing the guiding hole. The elastic seal adjusting mechanism is switchable between a compression state and a relaxation state. In the compression state, the abutting protrusion presses the pressing tab to cause an elastic deformation of one end of the main body facing away from the pressing tab so as to seal the guiding hole. In the relaxation state, the abutting protrusion removes pressure to the pressing tab, and the end of the main body facing away from the pressing tab is spaced apart from the guiding hole.

In some embodiments, an elastic member is provided at a middle of the end of the main body facing away from the pressing tab. The elastic member has one end facing the guiding hole. The main body has a peripheral portion protrudes radially from the elastic member. The peripheral portion defines an engaging groove, and the second housing is provided with an engaging post matching the engaging groove.

In some embodiments, the air control mechanism further includes a third housing connected to the driving motor through a screw connection. The third housing has a second chamber communicating with an exterior of the third housing. The second housing is detachably connected to an end of the third housing and is disposed at an end of the third housing facing away from the driving motor.

In some embodiments, at least one engaging member is provided at a periphery of the first housing. The at least one engaging member each has an engaging protrusion protrudes inward. A periphery of the second housing and a periphery of the third housing each defines a guiding groove matching the engaging member. The third housing is further provided with a buckle engaging the engaging protrusion.

In some embodiments, three engaging members are provided and uniformly spaced from each other along the periphery of the first housing.

According to embodiments of the present disclosure, a sphygmomanometer is provided. The sphygmomanometer includes a cuff and an air control mechanism according to any one of the above embodiments. The air control mechanism is connected to the cuff.

In comparison with the existing sphygmomanometer, the sphygmomanometer provided in the present disclosure has a simplified internal structure without requirements of the umbrella-shaped valve, the electromagnetic valve, the inflation valve and the like, which facilitates miniaturization design of the sphygmomanometer, reduces use of the electric energy, and metes the requirement of energy conservation and environmental protection. In addition, grooves and holes are used for air intake, so that the flexible pipes are not required for air transmission during inflation or deflation, which avoids the occurrence of air leakage from the pipes, blocking due to bending of the pipes and detaching of the pipes.

BRIEF DESCRIPTION OF THE DRAWINGS

In order to describe the technical solutions in the embodiments of the present disclosure more clearly, the accompanying drawings for description of the embodiments will be briefly introduced below. It should be appreciated that the accompanying drawings in the following description are merely some embodiments of the present disclosure, and other drawings may be conceivable from these drawings without creative effort for those skilled in the art.

DETAILED DESCRIPTION

Figure 1:
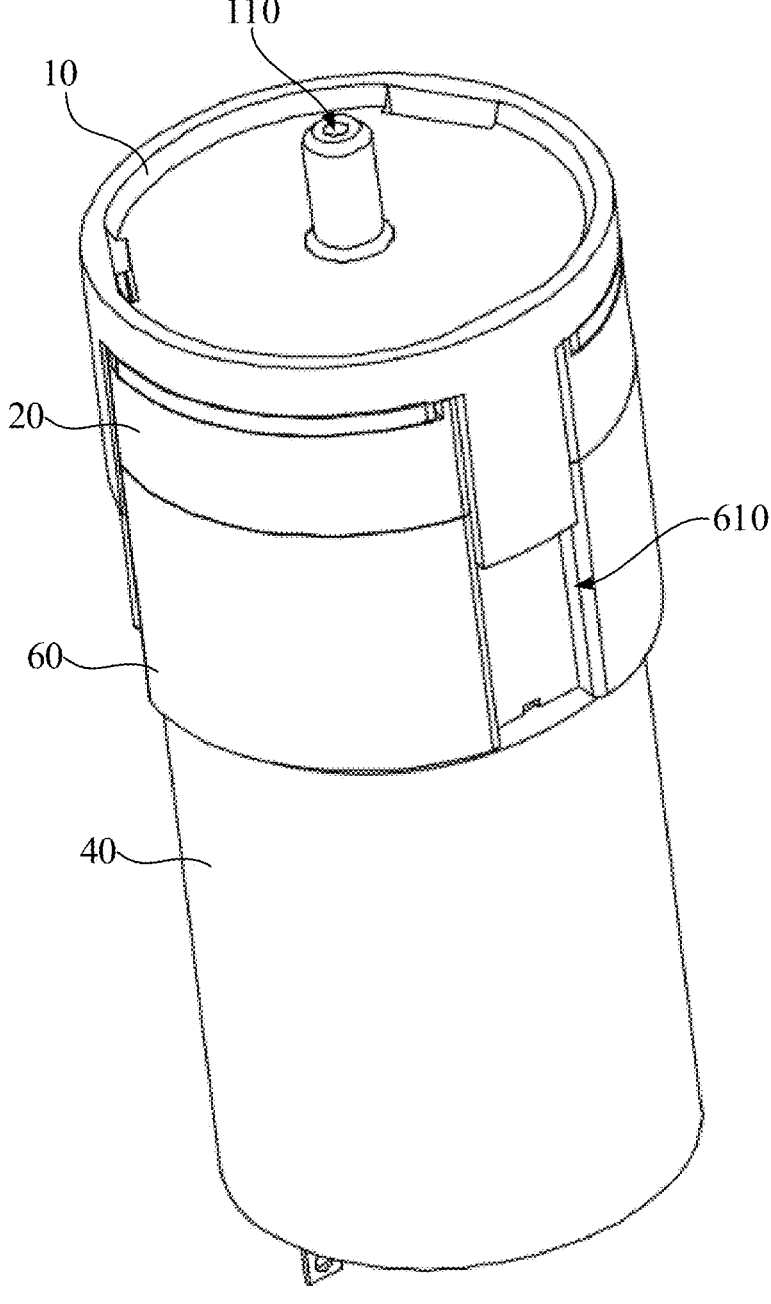
FIG. 1 is a schematic structural diagram of the sphygmomanometer of the present disclosure.
Figure 2:
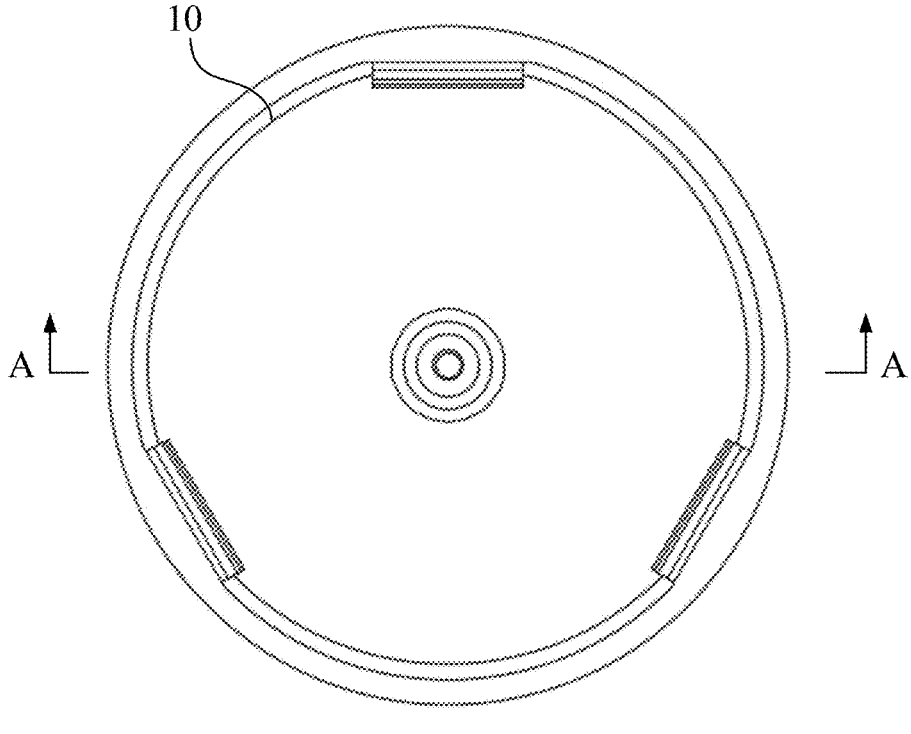
FIG. 2 is a top view of FIG. 1.

In order for those skilled in the art to better understand the technical solutions in the present disclosure, the technical solutions in the embodiments of the present disclosure will be clearly and exemplarily described below with reference to the drawings. Obviously, the described embodiments are only a part of the embodiments of the present disclosure, and not all embodiments. Based on the embodiments in the present disclosure, all other embodiments obtained by those skilled in the art without making creative works fall within the protection scope of the present disclosure.

It should be noted that when a component is referred to as being "fixed" or "disposed" to another component, it may be fixed or disposed to another component directly or indirectly; when a component is referred to as being "connected" to another component, it may be connected to another component directly or indirectly.

It is to be understood that the terms "length," "width," "up," "down," "front," "rear," "left," "right," "vertical," "horizontal," "top," "bottom," "inside," "outside," and other terms indicating the orientation or positional relationship are based on the orientation or positional relationship shown in the drawings. Such descriptions relating those terms are used for convenience of description of the present disclosure and simplification of description, rather than indicating or implying that the devices or components referred to must have a particular orientation, or be constructed or operated in a particular orientation, and are therefore not to be construed as limiting the present disclosure.

In addition, the terms "first" and "second" are used for descriptive purpose only, and cannot be understood as indicating or implying relative importance or implying the number of indicated technical features. Thus, the features defined as "first," "second" may explicitly or implicitly include one or more of the features. In the description of the present disclosure, "a plurality of," "a number of" means two or more, unless specifically defined otherwise.

It should be noted that the structure, scale, size, etc. shown in the drawings of this specification are only for cooperating with the contents disclosed in the specification, so as to be understood and read by those skilled in the art, rather than intending to limit the practical conditions of the present disclosure, and thus have no technical significance. Any modification of the structure, change of the ratio relationship, or adjustment of the size, without affecting the functions and the objectives achieved by the present disclosure, should fall within the protection scope of the present disclosure.

Referring to FIGS. 1 to 11, according to embodiments of the present disclosure, a sphygmomanometer is provided and includes a cuff and an air control mechanism. The air control mechanism is connected to the cuff and is configured to inflate or deflate the cuff for pressure measurement.

Referring to FIGS. 1 to 5, in some embodiments, the air control mechanism includes a first housing 10, a second housing 20, a piston 210, and an intake-exhaust mechanism 30. The first housing 10 has a flow passage 110. One end of the flow passage 110 is connected to the cuff. An end surface of the first housing 10 facing the second housing 20 defines a flow groove 130, and an end surface of the second housing 20 facing the first housing 10 defines a guiding groove 250. The piston 210 has at least one first chamber 220 communicating with the flow groove 130. The piston 210 is mounted to the second housing 20 and disposed between the first housing 10 and the second housing 20. The piston 210 defines an exhaust passage 240 extending along an axis of the piston 210 and communicating with the flow passage 110. A side surface of the piston 210 facing the first house 10 defines at least one stepped hole 260. The stepped hole 260 has one end communicating with the guiding groove 250, and one other end spaced apart from the flow groove 130. The piston 210 is provided with an elastic thin plate at a periphery of the stepped hole 260.

The intake and exhaust mechanism 30 is configured to intake airflow toward the flow passage 110 or exhaust airflow along the flow passage 110 to the exhaust passage 240. The intake-exhaust mechanism 30 is configured in such a way that, in an intake state, air in the first chamber 220 sequentially flows through the flow groove 130, presses against the elastic thin plate, flows through the stepped hole 260 and flows to the exhaust passage 240 through the guiding groove 250, and in an exhaust state, air sequentially flows through the flow passage 110 and the exhaust passage 240 to the guiding groove 250.

Firstly, for the air transmission, the present disclosure employs grooves and passages without using any flexible pipe, so as to avoid the defects of air leakage, unstable air pressure, complex structure, difficult detection and the like. In addition, the internal structure of the sphygmomanometer is simplified without using the umbrella-shaped valve, the electromagnetic valve, the air release valve and the like inside the first housing 10 and the second housing 20, which facilitates miniaturization design of the sphygmomanometer and meets the requirements of energy saving and environmental protection.

In some embodiments, the guiding groove 250 includes a guiding hole 2520 and a plurality of guiding units 2510 arranged around the guiding hole 2520 One end of the guiding hole 2520 communicates with the exhaust passage 240. and one other end of the guiding hole 2520 communicates with the intake-exhaust mechanism 30. The number of the guiding units 2510 is equal to the number of the first chambers 220, and is equal to the number of the flow grooves 130.

Specifically, three guiding units 2510, three flow grooves 130, and three first chambers 220 are provided. Compared with the conventional design with two first chambers 220, the present disclosure provides three first chambers 220 for the piston 210, which facilitates compression of the air to improve the intake efficiency of the sphygmomanometer. In other embodiments, there may be four first chambers 220, five first chambers 220, and the like. That is, the number of the first chambers 220 may be varied according to actual needs, and is not limited herein.

Figure 7:
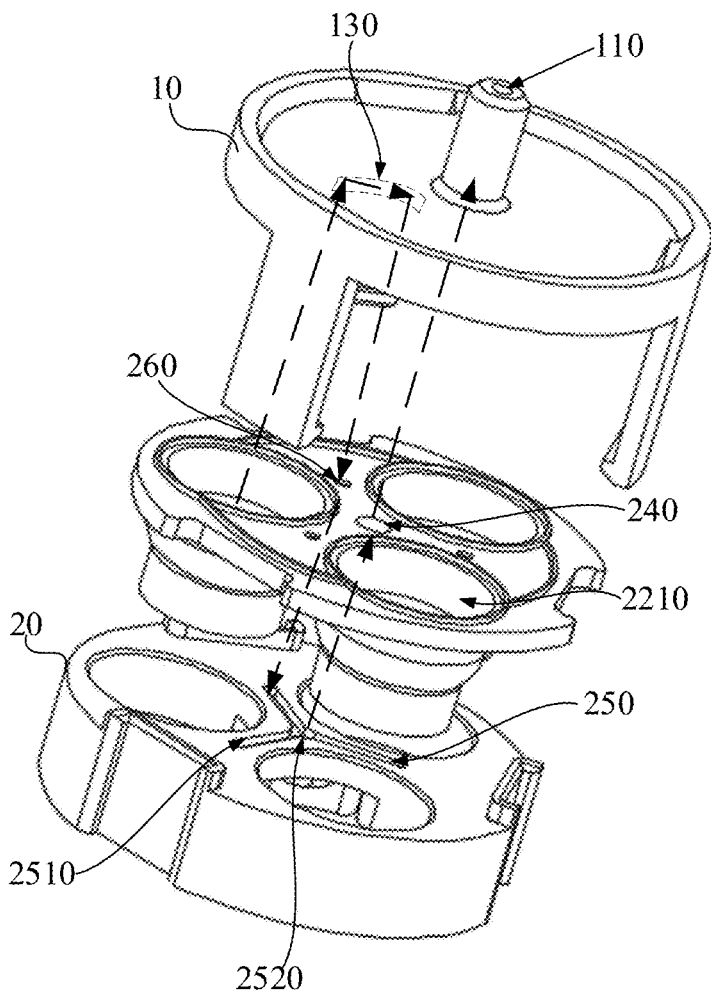
FIG. 7 is a schematic view of parts of the structure shown in FIG. 5.
Figure 8:
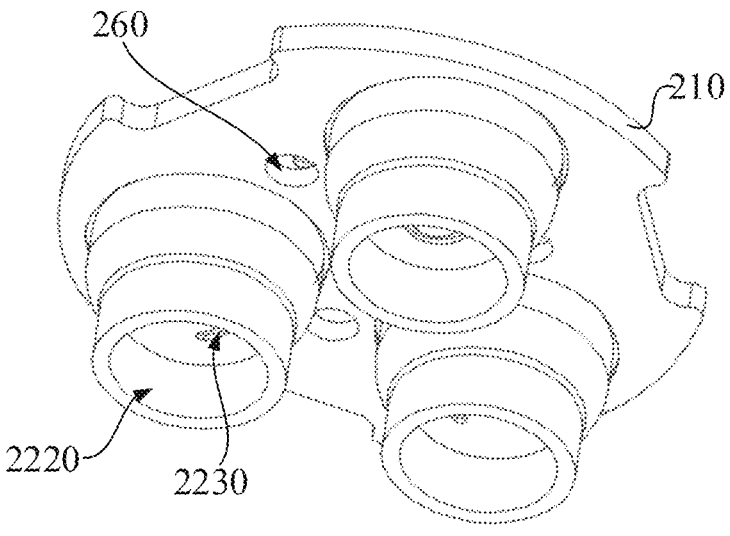
FIG. 8 is a schematic structural view of the piston shown in FIG. 7.
Figure 9:
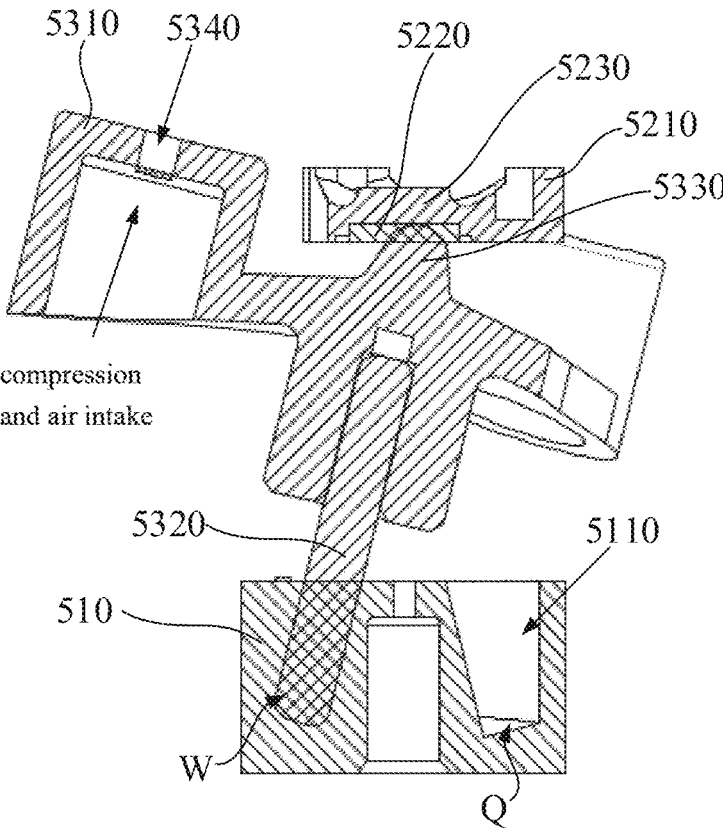
FIG. 9 is a sectional view of a seal adjusting mechanism in a certain state.
Figure 10:
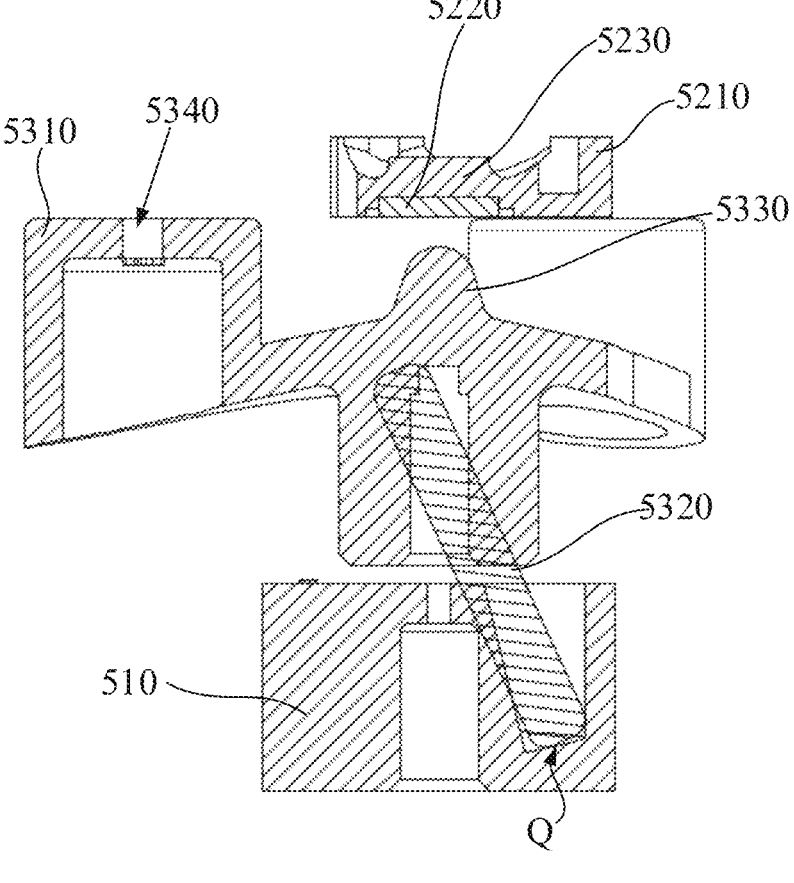
FIG. 10 is a sectional view of the seal adjusting mechanism in another state.
Figure 11:
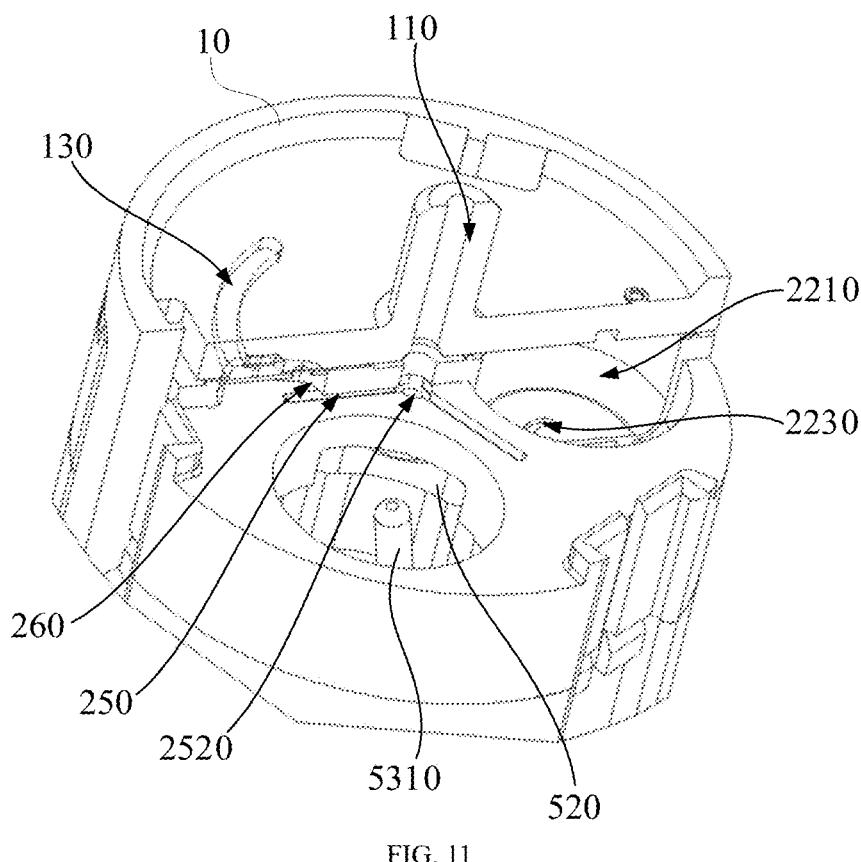
FIG. 11 is a partial cross-sectional view of the top of the sphygmomanometer shown in FIG. 1.

Further, the first chamber 220 includes an upper chamber 2210 and a lower chamber 2220 (refer to FIG. 7 and FIG. 8). The piston 210 is provided with a baffle plate in the middle of each first chamber 220. An arc-shaped vent 2230 is defined on the baffle plate and communicates with the upper chamber 2210 and the lower chamber 2220, respectively. During intake of the air, the compressed air in the lower chamber 2220 is transmitted to the upper chamber 2210 through the arc-shaped vent 2230, and the upper chamber 2210 communicates with the flow groove 130. The baffle plate is made from an elastic material, and deforms for air intake when being pressed.

The stepped hole 260 includes an upper hole disposed close to the first housing 10, and a lower hole disposed away from the first housing 10. The diameter of the upper hole is smaller than that of the lower hole. The piston 210 has an elastic thin plate defining the upper hole. An end of the flow groove 130 facing the stepped hole 260 is spaced apart from the upper hole. During intake of the air, when the air flows toward the stepped hole 260 through the flow groove 130, the elastic thin plate is compressed and deforms downward, the upper hole is depressed toward the lower hole to form a concave groove, so that the flow groove 130 communicates with the lower hole to allow the air flowing to the flow passage 110 through the stepped hole 260. During exhausting of the air, when the air flows from the flow passage 110 to the exhaust passage 240, and part of the air flows upward to the stepped hole 260 through the guiding groove 250, the elastic thin plate is pressed to abut against the inner wall of the first housing 10, and the flow groove 130 and the stepped hole 260 are not in communication with each other, so that the air flow cannot be recirculated, which is the reason why the air flows unidirectionally during intake.

Figure 3:
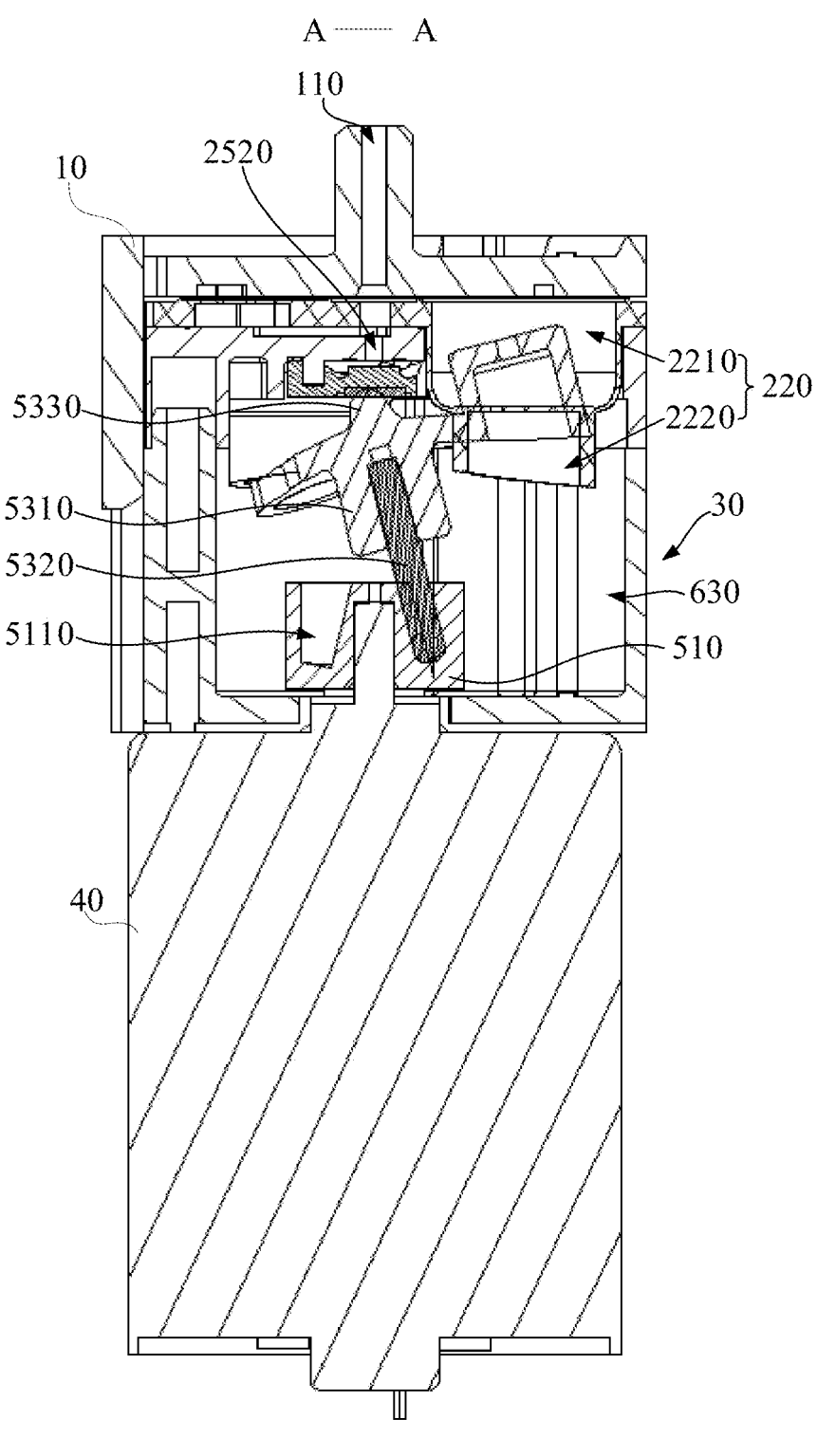
FIG. 3 is a sectional view taken from A-A of FIG. 2.
Figure 4:
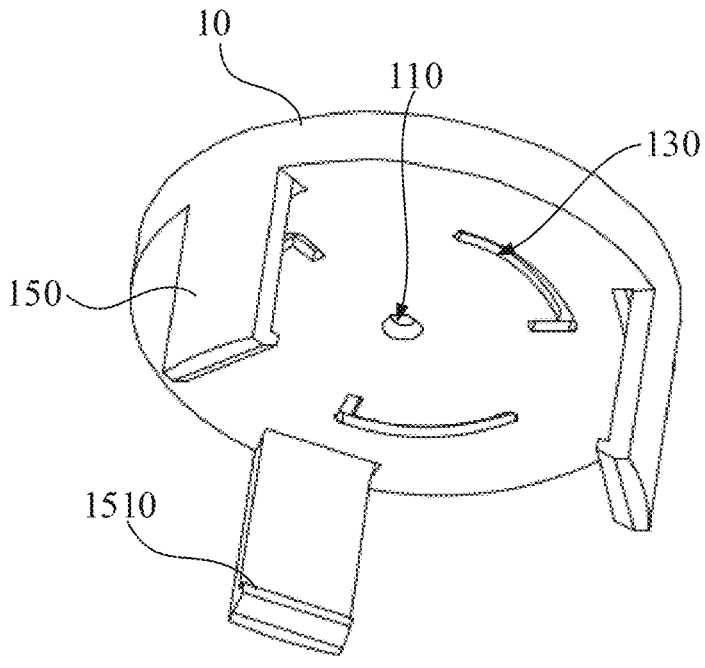
FIG. 4 is a schematic structural view of the first housing shown in FIG. 1.
Figure 5:
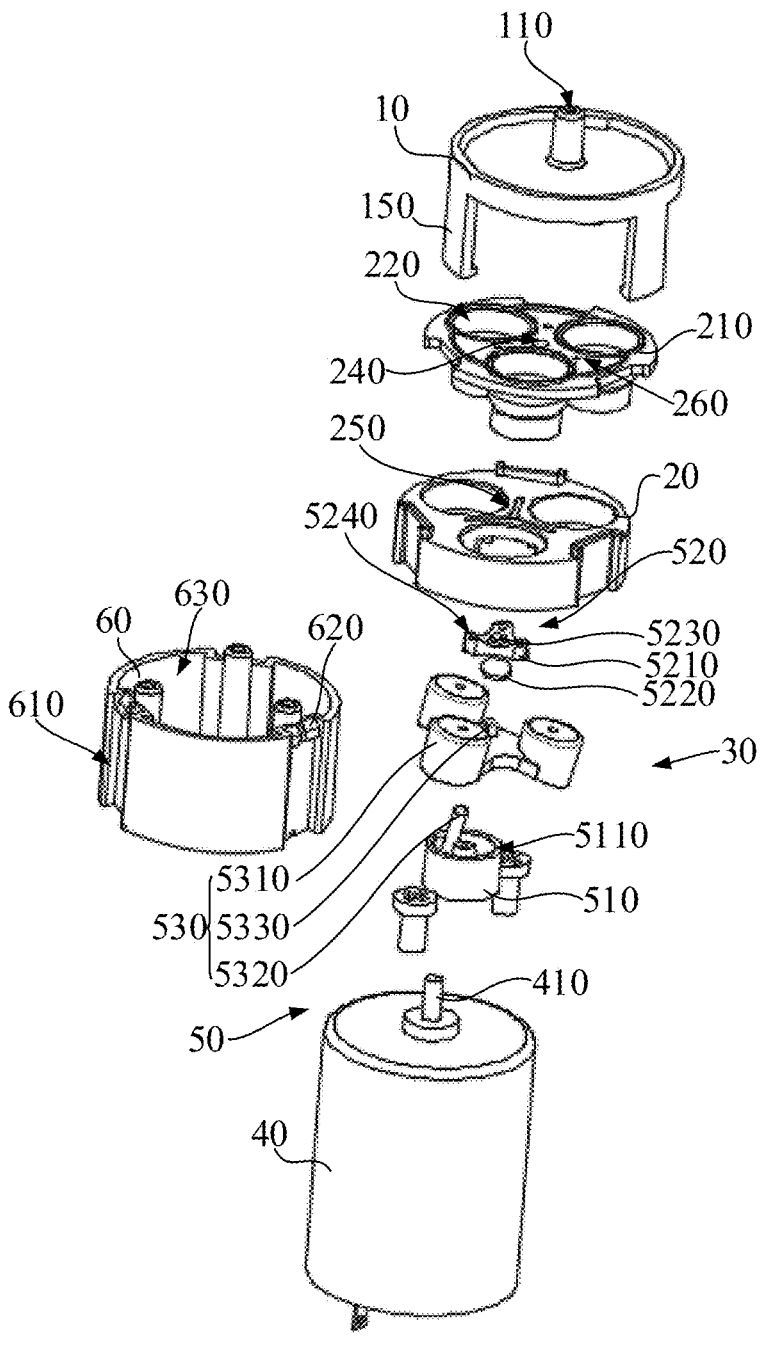
FIG. 5 is an exploded view of the sphygmomanometer shown in FIG. 1.

Referring to FIG. 3 to FIG. 5, the intake-exhaust mechanism 30 includes a drive motor 40 and a seal adjusting mechanism 50, and the drive motor 40 has an output shaft 410. The seal adjusting mechanism 50 includes an eccentric rotor 510 and an elastic seal adjusting mechanism 520. The eccentric rotor 510 has one end connected to the output shaft 410, and one other end provided with an annular installation groove 5110. The annular installation groove 5110 spirally extends along an axis of the eccentric rotor 510. A transmission wing 530 is provided between the eccentric rotor 510 and the elastic seal adjusting mechanism 520. The transmission wing 530 has one end received in the annular installation groove 5110 and slidably engaged with the annular installation groove 5110, and one other end facing the elastic seal adjusting mechanism 520. The elastic seal adjusting mechanism 520 has one end facing away from the transmission wing 530 and facing the guiding hole 2520. The transmission wing 530 is configured to be driven by the driving motor 40 in such a way that one end of the elastic sealing adjusting mechanism 520 seals the guiding hole 2520 or moves away from the guiding hole 2520.

Referring to FIG. 5 and FIG. 9 to FIG. 11, the transmission wing 530 includes a housing 5310 and a rotating column 5320 connected to the housing 5310. One end of the rotating column 5320 is inserted into the annular installation groove 5110. The driving motor 40 is configured to rotate the eccentric rotor 510 in such a way that the rotating column 5320 presses the housing 5310 to move upward or downward so that the elastic seal adjustment mechanism 520 seals the guiding hole 2520 or moves away from the guiding hole 2520.

In some embodiments, one end of the rotating column 5320 maybe spherically shaped to facilitate sliding of the rotating column 5320 within the annular installation groove 5110. For example, a clockwise spiral of the annular installation groove 5110 may result in a clockwise rotation of the driving motor 40, which moves the rotating column 5320 in a direction away from the driving motor 40, thereby moving the housing 5310 in a direction away from the driving motor 40. Similarly, if the driving motor 40 rotates counterclockwise, the housing 5310 is moved toward the driving motor 40.

In some embodiments, an end surface of the housing 5310 facing away from the rotating column 5320 is provided with an abutting protrusion 5330, and the elastic seal adjusting mechanism 520 includes a main body 5210 and a pressing tab 5220 disposed at a middle of the main body 5210. One end of the main body 5210 facing away from the pressing tab 5220 faces the guiding hole 2520. The elastic seal adjusting mechanism 520 is switchable between a compression state and a relaxation state. In the compression state, the abutting protrusion 5330 presses the pressing tab 5220 to cause an elastic deformation of one end of the main body 5210 facing away from the pressing tab 5220 so as to seal the guiding hole 2520. In the relaxation state, the abutting protrusion 5330 removes pressure to the pressing tab 5220, and the end of the main body 5210 facing away from the pressing tab 5220 is spaced apart from the guiding hole 2520.

The pressing tab 5220 may be made from a metal. One end of the pressing tab 5220 may be adhered to one end of the main body 5210. In the compression state, the abutting protrusion 5330 presses the pressing tab 5220, and the end of the main body 5210 facing away from the pressing tab 5220 is pressed to protrude upward, and moves toward one end of the guiding hole 2520 to close the guiding hole 2520 and thus the exhaust passage 240. In the relaxation state, the main body 5210 is elastically contracted and moves away from the flow passage 110.

Figure 6:
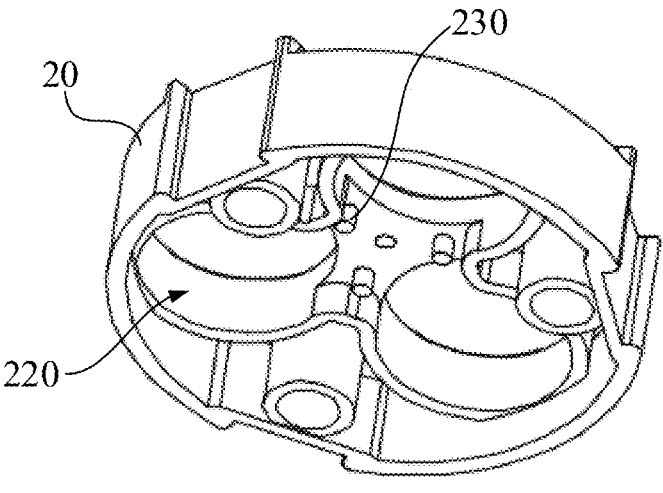
FIG. 6 is a schematic structural view of the second housing shown in FIG. 5.

Further referring to FIG. 5 and FIG. 6, an elastic member 5230 is provided at a middle of the end of the main body 5210 facing away from the pressing tab 5220. The elastic member 5230 has one end facing the guiding hole 2520. The main body 5210 has a peripheral portion protrudes radially from the elastic member 5230. The peripheral portion defines an engaging groove 5240, and the second housing 20 is provided with an engaging post 230 matching the engaging groove 5240.

Further, the housing 5310 includes three intake pistons, each intake piston defines a guiding passage 5340 and is inserted into the lower chamber 2220. The guiding passage 5340 has one end communicated with the lower chamber 2220, and one other end communicated with a second chamber 630 (which will be described below).

Referring to FIG. 7 to FIG. 11, the annular installation groove 5110 of the eccentric rotor 510 includes a bottom end Q and a top end W. When the rotating column 5320 is located at the top end W (refer to FIG. 9), the abutting protrusion 5330 presses the pressing tab 5220 to cause the elastic member 5230 to move upward and deform so as to press and seal the guiding hole 2520. When the rotating column 5320 is located at the bottom end Q (refer to FIG. 10), the abutting protrusion 5330 is spaced apart from the pressing tab 5220, a top end of the elastic member 5230 is spaced apart from a bottom surface of the second housing 20, and thus the guiding hole 2520 is spaced apart from the elastic member 5230, so that the air can flow from the elastic seal adjusting mechanism 520 to the second chamber 630 (which will be described below) through the guiding hole 2520, thereby realizing quick pressure release and air release.

Specifically, the air intake process of the cuff is as follows. During intake of the air, the driving motor 40 rotates clockwise to drive the output shaft 410 to rotate clockwise. When rotating with the annular installation groove 5110, the rotating column 5320 presses the housing 5310 to move upward, the abutting protrusion 5330 moves upward to press against the pressing tab 5220, and the pressing tab 5220 presses against the elastic member 5230 to cause the elastic member 5230 to protrude upward and deform so as to press against the guiding hole 2520, thereby sealing the exhaust passage 240. Meanwhile, the driving motor 40 continues to rotate clockwise, and then takes the pressing piece 5220 as a center, drives the three intake pistons of the housing 5310 to reciprocate for air intake and compression in the lower chamber 2220 in turn. During intake and compression of the air, for example, take one intake piston as an example, in an initial state, the intake piston is spaced apart from the baffle between the upper chamber 2210 and the lower chamber 2220, leaving a certain space for air compression, and with the rotation of the drive motor 40, the intake piston compress the air of the space, the intake piston presses a lower end surface of the baffle or the baffle deforms and moves upward, so that all the air in the space flows to the upper chamber 2210 through the arc-shaped vent 2230. At this time, the lower chamber 2220 is almost vacuum, so the air outside the housing 5310 will enter the lower chamber 2220 through the guiding passage 5340 of the intake piston for balance of the air pressure, thereby pushing the housing 5310 back to the initial state. That is, the air intake and compression is repeated with the rotation of the drive motor 40, and according to the principle of air pressure balance, the intake air flows unidirectionally from bottom to top.

The air in the upper chamber 2210 flows through the flow groove 130, the stepped hole 260, the guiding groove 250, and the guiding hole 2520 in sequence to the exhaust passage 240, and a lower inlet of the exhaust passage 240 is sealed by the pressing tab 5220. Therefore, the air flows upward into the flow passage 110 and then is transmitted to the cuff to inflate the cuff. With the continuous rotation of the driving motor 40, under the abutment of the abutment protrusion 5330, the three intake pistons in turn bring the air into the lower chamber 2220 and compress the air in the lower chamber 2220 to inflate the cuff. When the air pressure in the cuff reaches a desirable value, the pressing tab 5220 is held to close the exhaust passage 240 for pressure maintaining. When the pressure needs to be released, the driving motor 40 rotates counterclockwise, and the output shaft 410 rotates counterclockwise to move the rotating column 5320 downward, and meanwhile the air flows through the flow passage 110 and the exhaust passage 240 and then is discharged through the guiding hole 2520, thereby realizing quick pressure release.

In some embodiments, the elastic seal adjusting mechanism 520 and the second housing 20 are detachably connected to each other. In this way, after a long-time use, the elastic seal adjusting mechanism 520, which is damaged or whose elastic effect is reduced, can be removed and replaced.

In some embodiments, the sphygmomanometer further includes a third housing 60 connected to the driving motor 40 through a screw connection. The third housing 60 has a second chamber 630 communicating with an exterior of the third housing 60. The second housing 20 is detachably connected to an end of the third housing 60 and is disposed at an end of the third housing 60 facing away from the driving motor 40. During exhausting of the air, the air flows through the flow passage 110, the exhaust passage 240, and the guiding hole 2520 to the second chamber 630 which communicates with the outside, thereby realizing pressure release.

Further, the second housing 20 and the third housing 60 may be detachably connected by a plurality of positioning pins, for example, two or three positioning pins. The number of the positioning pins is not limited herein.

In some embodiments, at least one engaging member 150 is provided at a periphery of the first housing 10. The at least one engaging member 150 each has an engaging protrusion 1510 protrudes inward. A periphery of the second housing 20 and a periphery of the third housing 60 each defines a guiding groove 610 matching the engaging member 150. The third housing 60 is further provided with a buckle 620 engaging the engaging protrusion 1510.

In some embodiments, three engaging members 150 are provided, and arranged at intervals along the periphery of the first housing 10.

For example, the engaging member 150 is an elastic sheet. During connection of the first housing 10 and the third housing 60, the first housing 10 is pressed so that the engaging protrusion 1510 of the engaging member 150 engages with the buckle 620. In this way, the connection between the first housing 10 and the third housing 60 is completed in a simple way, and it is convenient to detach the first housing 10 from the third housing for maintenance of the internal structure of the first housing 10, the second housing 20 and the third housing 60.

The air control mechanism provided by the present disclosure has a simplified internal structure without requirements of the umbrella-shaped valve, the air release valve, the electromagnetic valve and the like, and employs flow passage design for air intake and discharge without using the flexible pipes. This realizes a miniaturized design of the sphygmomanometer, and improves detection accuracy of the sphygmomanometer.

The above description of the disclosed embodiments enables those skilled in the art to realize or use the present disclosure. Various modifications to these embodiments will be apparent to those skilled in the art, and the general principles defined herein may be practiced in other embodiment without departing from the spirit or scope of the present disclosure. Accordingly, the present disclosure will not be limited to the embodiments shown herein, but will be accorded with the widest scope consistent with the principles and novel features disclosed herein.

What is claimed is:

1. An air control mechanism, comprising:
a first housing having a flow passage configured to be connected to a cuff;
a second housing connected to the first housing, wherein an end surface of the first housing facing the second housing defines a flow groove, an end surface of the second housing facing the first housing defines a guiding groove;
a tower-shaped piston having at least one first chamber in communication with the flow groove, wherein the piston is mounted to the second housing and disposed between the first housing and the second housing, the piston defines an exhaust passage extending along an axis of the piston and communicating with the flow passage, a side surface of the piston facing the first housing defines at least one stepped hole, the stepped hole has one end communicating with the guiding groove, and one other end spaced apart from the flow groove, and the piston is provided with an elastic thin plate at a periphery of the stepped hole;
an intake-exhaust mechanism configured to intake airflow toward the flow passage or exhaust airflow along the flow passage to the exhaust passage, wherein the intake-exhaust mechanism is configured in such a way that in an intake state, air in the first chamber sequentially flows through the flow groove, presses against the elastic thin plate, flows through the stepped hole and flows to the exhaust passage through the guiding groove, and in an exhaust state, air sequentially flows through the flow passage and the exhaust passage to the guiding groove.

2. The air control mechanism according to claim 1, wherein the guiding groove comprises a guiding hole and a plurality of guiding units arranged around the guiding hole, the guiding hole has one end communicating with the exhaust passage and one other end communicating with the intake-exhaust mechanism; and
wherein a number of the guiding units is equal to a number of the first chambers, and is equal to a number of the flow grooves.

3. The air control mechanism according to claim 2, wherein the intake-exhaust mechanism includes a drive motor and a seal adjusting mechanism, and the drive motor has an output shaft; and
wherein the seal adjusting mechanism includes an eccentric rotor and an elastic seal adjusting mechanism, and the eccentric rotor has one end connected to the output shaft, and one other end provided with an annular installation groove, the annular installation groove spirally extends along an axis of the eccentric rotor, a transmission wing is provided between the eccentric rotor and the elastic seal adjusting mechanism, the transmission wing has one end received in the annular installation groove and slidably engaged with the annular installation groove, and one other end facing the elastic seal adjusting mechanism, the elastic seal adjusting mechanism has one end facing away from the transmission wing and facing the guiding hole, and the transmission wing is configured to be driven by the driving motor in such a way that one end of the elastic sealing adjusting mechanism seals the guiding hole or moves away from the guiding hole.

4. The air control mechanism according to claim 3, wherein the transmission wing comprises a housing and a rotating column connected to the housing; and
wherein the rotating column has one end inserted into the annular installation groove, and the driving motor is configured to rotate the eccentric rotor in such a way that the rotating column presses the housing to move upward or downward so that the elastic seal adjustment mechanism seals the guiding hole or moves away from the guiding hole.

5. The air control mechanism according to claim 4, wherein an end surface of the housing facing away from the rotating column is provided with an abutting protrusion;
wherein the elastic seal adjusting mechanism includes a main body and a pressing tab disposed at a middle of the main body, the main body has one end facing away from the pressing tab and facing the guiding hole; and
wherein the elastic seal adjusting mechanism is switchable between a compression state and a relaxation state, and in the compression state, the abutting protrusion presses the pressing tab to cause an elastic deformation of one end of the main body facing away from the pressing tab so as to seal the guiding hole, and in the relaxation state, the abutting protrusion removes pressure to the pressing tab, and the end of the main body facing away from the pressing tab is spaced apart from the guiding hole.

6. The air control mechanism according to claim 5, wherein an elastic member is provided at a middle of the end of the main body facing away from the pressing tab, the elastic member has one end facing the guiding hole; and
wherein the main body has a peripheral portion protrudes radially from the elastic member, the peripheral portion defines an engaging groove, and the second housing is provided with an engaging post matching the engaging groove.

7. The air control mechanism according to claim 3, further comprising a third housing connected to the driving motor through a screw connection, the third housing has a second chamber communicating with an exterior of the third housing; and wherein the second housing is detachably connected to an end of the third housing and is disposed at an end of the third housing facing away from the driving motor.

8. The air control mechanism according to claim 7, wherein at least one engaging member is provided at a periphery of the first housing, the at least one engaging member each has an engaging protrusion protrudes inward; and wherein a periphery of the second housing and a periphery of the third housing each defines a guiding groove matching the engaging member, and the third housing is further provided with a buckle engaging the engaging protrusion.

9. The air control mechanism according to claim 8, wherein three engaging members are provided, and arranged at intervals along the periphery of the first housing.

10. A sphygmomanometer, comprising:

a cuff; and an air control mechanism connected to the cuff, wherein the air control mechanism comprises:

a first housing having a flow passage configured to be connected to a cuff;

a second housing connected to the first housing, wherein an end surface of the first housing facing the second housing defines a flow groove, an end surface of the second housing facing the first housing defines a guiding groove;

a tower-shaped piston having at least one first chamber in communication with the flow groove, wherein the piston is mounted to the second housing and disposed between the first housing and the second housing, the piston defines an exhaust passage extending along an axis of the piston and communicating with the flow passage, a side surface of the piston facing the first housing defines at least one stepped hole, the stepped hole has one end communicating with the guiding groove, and one other end spaced apart from the flow groove, and the piston is provided with an elastic thin plate at a periphery of the stepped hole;

an intake-exhaust mechanism configured to intake airflow toward the flow passage or exhaust airflow along the flow passage to the exhaust passage, wherein the intake-exhaust mechanism is configured in such a way that in an intake state, air in the first chamber sequentially flows through the flow groove, presses against the elastic thin plate, flows through the stepped hole and flows to the exhaust passage through the guiding groove, and in an exhaust state, air sequentially flows through the flow passage and the exhaust passage to the guiding groove.

* * * * *